United States Patent
Childers, Jr. et al.

(10) Patent No.: US 6,828,324 B2
(45) Date of Patent: Dec. 7, 2004

(54) BRANCHED ADAMANTYL AND NORADAMANTYL ARYL-AND ARALKYLPIPERAZINES WITH SEROTONIN 5-HT$_{1A}$ ACTIVITY

(75) Inventors: Wayne E. Childers, Jr., New Hope, PA (US); Horace Fletcher, III, Pottstown, PA (US); Magid A. Abou-Gharbia, Exton, PA (US); John P. Yardley, King of Prussia, PA (US)

(73) Assignee: Wyeth, Madison, NJ (US)

(*) Notice: Subject to any disclaimer, the term of this patent is extended or adjusted under 35 U.S.C. 154(b) by 0 days.

(21) Appl. No.: 10/783,109

(22) Filed: Feb. 20, 2004

(65) Prior Publication Data

US 2004/0162430 A1 Aug. 19, 2004

Related U.S. Application Data

(63) Continuation of application No. 09/706,683, filed on Nov. 6, 2000
(60) Provisional application No. 60/219,348, filed on Nov. 18, 1999, and provisional application No. 60/228,820, filed on Nov. 12, 1999.

(51) Int. Cl.$^7$ ................... A61K 31/495; A61K 31/506; C07D 295/15; C07D 403/04
(52) U.S. Cl. ................ 514/252.02; 514/252.11; 514/252.12; 514/252.14; 514/253.01; 514/255.03; 544/238; 544/295; 544/357; 544/360; 544/380
(58) Field of Search ................. 544/295, 380, 544/360, 357, 238; 514/252.12, 252.14, 255.03, 253.01, 252.02, 252.11

(56) References Cited

U.S. PATENT DOCUMENTS

| | | |
|---|---|---|
| 3,717,634 A | 2/1973 | Wu et al. |
| 4,001,223 A | 1/1977 | Sugimoto et al. |
| 4,202,898 A | 5/1980 | Depoortere |
| 4,797,489 A | 1/1989 | Abou-Gharbia et al. |
| 4,873,331 A | 10/1989 | Childers, Jr. et al. |
| 4,882,432 A | 11/1989 | Abou-Gharbia et al. |
| 4,988,814 A | 1/1991 | Abou-Gharbia et al. |
| 5,254,552 A | 10/1993 | Abou-Gharbia et al. |
| 5,340,812 A | 8/1994 | Cliffe |
| 5,380,725 A | 1/1995 | Abou-Gharbia et al. |
| 5,420,278 A | 5/1995 | Cliffe |
| 5,482,940 A | 1/1996 | Abou-Gharbia et al. |
| 5,486,518 A | 1/1996 | Yardley et al. |
| 5,519,025 A | 5/1996 | Yardley et al. |

FOREIGN PATENT DOCUMENTS

| | | |
|---|---|---|
| EP | 395 313 | 10/1990 |
| EP | 512 755 B1 | 12/1994 |
| EP | 900 792 | 3/1999 |
| GB | 2218988 | 5/1989 |

OTHER PUBLICATIONS

Mucke, Hermann A.M. "Repinotan", Current Opinion in CPNS Investigational Drugs, 1(5), 621–628 (1999).
Rasmussen, K., Annual Reports in Med. Chemistry, 30, Academic Press, NY, 1–9 (1995).
Schaus, J.M., Annual Reports in Med. Chemistry, 33, Academic Press, NY, 21–30 (1998).
Holt, W.F., et al., Neuroprotection in CNS Diseases, Marcel Dekker, NY 87–119 (1997).
Engelsen, B., et al., Neurotoxicity of Excitatory Amino–Acids, Raven Press, NY 311–322 (1990).
Ince et al., Rev. Contemp. Pharmacother., 8, 195–212 (1997).
Meldrum, B., Prog. Brain Research., 116, 441–458 (1998).
Koroshetz & Moskowitz, Trends in Pharmacol. Sci., 17, 227–233 (1996).
Dunn, C.D.R., Scrip Reports, PJB Publications, Richmond (1995) Chapter Two, 61–90, Chapter Four, 149–159.
Arowsmith, J.E. et al., Stroke, 29, 2357–2362 (1998).
DeVry, Psychopharmacology, 121, 1–26 (1995).
Matsuyama, S., Brain Research, 728, 175–180 (1996).
DeVry, Drugs of the Future, 22, 341–349 (1997).
Schechter et al., Serotonin, 2(7), 299–309 (1997).
Lazareno et al., Br. J. Pharmacol., 109, 1120–27 (1993).
Coyle, Harvard Rev. Psychiatry, 3(5), 241–253 (1996).
Lucki et al., J. Pharma. & Experimental Ther., 228(1), 133–139 (1983).
Smith, L.M. et al., Pharmacol. Biochem Behavior, 24, 1513–19 (1986).

*Primary Examiner*—Emily Bernhardt
(74) *Attorney, Agent, or Firm*—Kimberly R. Hild

(57) ABSTRACT

This invention provides compounds and methods using them to provide neuroprotection and prevent or limit processes of neurodegeneration in mammals, including Alzheimer's Disease, Huntington's Disease, Parkinson's Disease, AIDS dementia, retinal disease, diabetic peripheral neuropathy, multiple sclerosis, stroke, acute thromboembolic stroke, focal ischemia, global ischemia, transient ischemic attack, ischemia resulting from surgery, head trauma, spinal trauma, hypoxia, fetal hypoxia, and neuroprotection. The compounds having the structure:

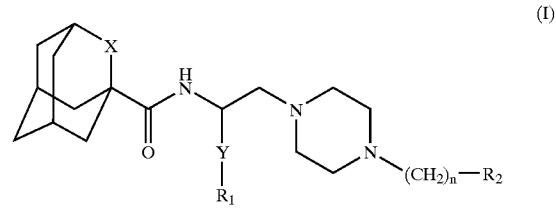

(I)

wherein X is —CH$_2$— or a bond; Y is —(CH$_2$)$_m$— or —(CH$_2$)—O—(CH$_2$)—; m 0 or 1; n is 0 or 1; R$_1$ and R$_2$ are independently selected from optionally substituted aryl or heteroaryl; the optical isomers and the pharmaceutically acceptable salts thereof.

13 Claims, No Drawings

BRANCHED ADAMANTYL AND NORADAMANTYL ARYL- AND ARALKYLPIPERAZINES WITH SEROTONIN 5-HT$_{1A}$ ACTIVITY

This application is a continuation of U.S. application Ser. No. 09/706,683, filed Nov. 6, 2000, pending, which claims the benefit of U.S. Provisional Application No. 60/228,820, filed Nov. 12, 1999 and U.S. Provisional Application No. 60/219,348, filed Nov. 18, 1999.

This invention relates to novel branched adamantyl, noradamantyl aryl and aralkylpiperazines having serotonin 5-HT$_{1A}$ activity. More particularly, the present invention relates to compounds and methods using them to provide neuroprotection and prevent, inhibit or limit processes of neurodegeneration in mammals.

INTRODUCTION

Compounds having selective agonist and partial agonist activity at the 5-HT$_{1A}$ receptor have established a presence in the marketplace as effective anxiolytic agents (buspirone, Buspar®, U.S. Pat. No. 3,717,634). Evidence generated over the past 20 years supports the hypothesis that 5-HT$_{1A}$ agonists and partial agonists may find use in the treatment of several diseases such as anxiety, depression, schizophrenia, sexual dysfunction, cognitive deficits resulting from neurodegenerative diseases like Alzheimer's Disease, nausea and vomiting, sleep disorders, pain, obesity, pain, addiction/withdrawl and in the treatment of prostate cancer (for recent reviews, see: Rasmussen, K. and Rocco, V. P., Recent Progress in Serotonin (5-HT)$_{1A}$ Receptor Modulators, In: *Annual Reports in Medicinal Chemistry, Volume* 30, Bristol, J. A., ed., Academic Press, New York, 1995, pp. 1–9; Schaus, J. M. and Bymaster, F. P., Latest Developments in Serotonin Receptor Modulation, In: *Annual Reports in Medicinal Chemistry, Volume* 33, Bristol, J. A., ed., Academic Press, New York, 1998, pp. 21–30).

More recent evidence now indicates that 5-HT$_{1A}$ agonists and partial agonists act in other disease states and conditions by virtue of their ability to inhibit the release of glutamate. 5-HT$_{1A}$ agonists and partial agonists may be used to treat conditions arising from the dysfunction of the glutamate neurotransmitter system or the aberrant release of glutamate.

Glutamate is the predominant neurotransmitter in the central nervous system and it plays an important role in neuroplasticity. As such, excessive extracellular levels of glutamate have been associated with the pathophysiology of both acute neurodegenerative disorders such as stroke, transient ischemic attack and spinal/brain trauma, as well as chronic neurodegenerative disorders such as epilepsy, Alzheimer's Disease, amyotrophic lateral sclerosis, Huntington's Disease, Parkinson's Disease, AIDS dementia and retinal diseases (Holt, W. F. et al., Glutamate in Health and Disease: The Role of Inhibitors. In: *Neuroprotection in CNS Diseases*. Bar, P. R. and Beal, M. F., ed., Marcel Dekker, Inc., New York 1997, pp. 87–119; Engelsen, B. A. et al., Alterations in Excitatory Amino Acid Transmitters in Human Neurological Disease and Neuropathology. In: *Neurotoxicity of Excitatory Amino Acids*. Guidotti, A., ed., Raven Press Ltd., New York 1990, pp. 311–332; Ince, P. G. et al., The Role of Excitotoxicity in Neurological Disease. *Res. Contemp. Pharmacother.* 1997, 8, 195–212; Meldrum, P. S. The Glutamate Synapse as a Therapeutical Target: Perspective for the Future. *Prog. Brain. Res.* 1998, 441–458). Compounds which inhibit or attenuate the release of glutamate represent potential neuroprotective agents for the treatment of ischemia resulting from stroke, transient ischemic attack, brain/spinal trauma and fetal hypoxia (Koroshetz, W. J. and Moskowitz, M. A., Emerging Treatment for Stroke in Humans. *Trends in Pharmacol. Sci* 1996, 17, 227–233; Dunn, C. D. R. Stroke: Trends, Treatments and Markets. *Scrip Reports*, PJB Publications, Richmond 1995). Ischemia can also result from surgery where the blood flow must be halted for a period of time (e.g., cardiac by-pass surgery) due to the resulting anoxia and hypoglycemia (Arrowsmith, J. E. et al., Neuroprotection of the Brain During Cardiopulmonary Bypass. A Randomized Trial of Remacemide During Coronary Artery Bypass in 171 Patients, *Stroke* 1998, 29, 2357–2362, and references cited within).

Serotonin 5-HT$_{1A}$ receptors are located in brain areas which are highly sensitive to ischemia, such as the hippocampus and cerebral cortex. Activation of this receptor subtype results in neuronal hyperpolarization and a concomitant inhibition of neuronal activity (DeVry, J. 5-HT$_{1A}$ Receptor Agonists: Recent Developments and Controversial Issues. *Psychopharmacology* 1995, 121, 1–26). Moreover, it has been demonstrated that 5HT$_{1A}$ receptor agonists and partial agonists are able to attenuate glutamate release, most likely through activation of 5-HT$_{1A}$ receptors located on glutamatergic terminals (Matsuyama, S. et al., Regulation of Glutamate Release via NMDA and 5HT$_{1A}$ Receptors in Guinea Pig Dentate Gyrus. *Brain Res.* 1996, 728, 175–180) and that a number of 5-HT$_{1A}$ agonists and partial agonists exert neuroprotective properties in vivo (DeVry, J. et al., BAYx3702, *Drugs of the Future* 1997, 22, 341–349, and references cited within).

Therefore, in addition to its well established potential therapeutic applications, compounds which possesses 5-HT$_{1A}$ agonist or partial agonist activity may be used as neuroprotective agents as well as a means for treating psychosis.

Preclinical models, neurochemical hypotheses and brain localization have predicted a number of potential therapeutic targets for serotonin 5-HT$_{1A}$ antagonists as well. These targets include the cognitive deficits observed in Alzheimer's Disease, anxiety, depression, schizophrenia and urinary incontinence (for a review see Schechter, L. E. and Kelly, M. G., An Overview of 5-HT$_{1A}$ Receptor Antagonists: Historical Perspective and Therapeutic Targets, in *Serotonin—Current Drugs ID Research Alert* 1997, 2, 299–309).

DESCRIPTION OF THE INVENTION

In accordance with this invention, there is provided a set of novel compounds, including their enantiomers, which have activity as serotonin 5-HT$_{1A}$ agonists, partial agonists and antagonists. Compounds of the present invention are described by the formula I:

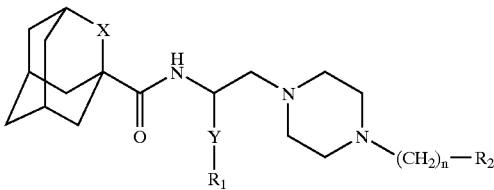

(I)

wherein:

X is selected from —CH$_2$— or a chemical bond;

Y is selected from —(CH$_2$)$_m$— or CH$_2$)—O—(CH$_2$)—;

m is selected from the integer 0 or 1;

n is selected from the integer 0 or 1;

R$_1$ and R$_2$ are independently selected from the group consisting of aryl or heteroaryl of from 5–10 atoms optionally substituted with F, Cl, Br, I, —OH, —NH$_2$, —CO$_2$H, —CO$_2$—C$_1$-C$_6$ alkyl, —CN, —NO$_2$, C$_1$-C$_6$ alkyl, C$_2$-C6 alkenyl, C$_2$-C$_6$ alkynyl, C$_1$-C$_6$ perhaloalkyl, OR$_3$, or C$_1$-C$_6$ perhaloalkoxy;

R$_3$ is selected from the group consisting of H, C$_1$-C$_6$ alkyl, C$_2$-C$_6$ alkenyl, C$_2$-C$_6$ alkynyl, C$_6$-C$_{10}$ aryl, mono or bicyclic heteroaryl, C$_7$-C$_{14}$ aralkyl, and mono or bicyclic heteroaralkyl, where the aryl or heteroaryl group is optionally substituted with one to three substituents independently selected from the group consisting of F, Cl, Br, I, CN, —NH$_2$, —NO$_2$, —OH, alkyl, C$_2$-C$_6$ alkenyl, C$_2$-C$_6$ alkynyl, C$_1$-C$_6$ perhaloalkyl, C$_1$-C$_6$ alkoxy, and C$_1$-C$_6$ perhaloalkoxy;

the optical isomers;

and the pharmaceutically acceptable salts thereof.

The term C$_6$-C$_{10}$ aryl includes phenyl and naphthyl. Monocyclic heteroaryl means a 5–6 membered heteroaryl group having from 1–3 heteroatoms selected independently from N, O, and S, such as pyridine, pyrrole, thiophene, furan, imidazole, oxazole, pyrimidine, pyridazine, pyrazine, thiazole and oxathiazole. Bicyclic heteroaryl includes phenyl fused to a monocyclic 5–6 membered heteroaryl group or a 5–6 membered heteroaryl group fused to another 5–6 membered heteroaryl group, including, but not limited to indole, quinoline, isoquinoline, benzofuran, benzodioxan, benzothiophene, benzimidazole, naphthyridine, and imidazopyridine. The term C$_7$-C$_{14}$ aralkyl means a C$_1$-C$_4$ alkyl group having a phenyl or naphthyl group as a substituent, and the term heteroaralkyl means a C$_1$-C$_4$ alkyl group having a mono or bicyclic heteroaryl group as defined above as a substituent.

Among the preferred compounds of this invention are those of the formula:

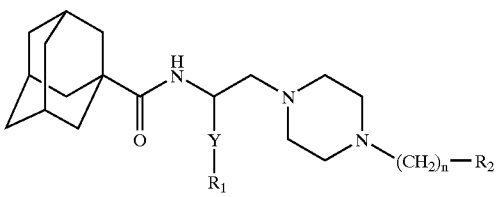

Y is selected from —(CH$_2$)$_m$— or —(CH$_2$)—O—(CH$_2$)—;

m is selected from the integer 0 or 1;

n is selected from the integer 0 or 1;

R$_1$ is phenyl optionally substituted with F, Cl, Br, I, —H, —NH$_2$, —CO$_2$H, —CO$_2$—C$_1$-C$_6$ alkyl, —CN, —NO$_2$, C$_1$-C$_6$ alkyl, C$_1$-C$_6$ alkoxy, C$_2$-C$_6$ alkenyl, C$_2$-C$_6$ alkynyl, C$_1$-C$_6$ perhaloalkyl or C$_1$-C$_6$ perhaloalkoxy;

R$_2$ is selected from phenyl, napthyl, piperazinyl, pyridine, thiophene, furan, imidazole, oxazole, pyrrole, pyrimidine, pyridazine, pyrazine, thiazole or oxathiazole;

the optical isomers;

and the pharmaceutically acceptable salts thereof.

Further preferred compounds of this invention are those of the formula:

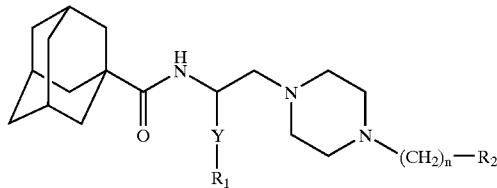

Y is selected from —CH$_2$—;

m is selected from the integer 0 or 1;

n is selected from the integer 0 or 1;

R$_1$ is phenyl optionally substituted with F, Cl, Br, I, —H, —NH$_2$, —CO$_2$H, —CO$_2$—C$_1$-C$_6$ alkyl, —CN, —NO$_2$, C$_1$-C$_6$ alkyl, C$_2$-C$_6$ alkenyl, C$_2$-C$_6$ alkynyl, C$_1$-C$_6$ perhaloalkyl, or C$_1$-C$_6$ perhaloalkoxy;

R$_2$ is phenyl or pyrimidinyl;

the optical isomers or a pharmaceutically acceptable salt thereof.

Optical isomers of the invention compounds can be selectively synthesized or separated using conventional procedures known to those skilled in the art of organic synthesis.

The pharmaceutically acceptable salts of the invention compounds include the conventional acid addition salts which are formed from an invention compound and a pharmaceutically acceptable organic or inorganic acid. The acid addition salts include, but is not limited to, the acetate, adipate, alginate, aspartate, benzoate, benzenesulfonate, bisulfate, butyrate, citrate, camphorate, camphorsulfonate, dodecylsulfate, ethanesulfonate, fumarate, glycerophosphate, phosphate, hemisulfate, hydrochloride, hydrobromide, hydroiodide, lactate, maleate, methanesulfonate, nicotinate, oxalate, pamoate, pectinate, pivalate, propionate, succinate, tartrate, and tosylate. Also the basic nitrogen-containing groups may be quaternized with such agents as lower alkyl halides, dialkyl sulfates, long chain halides such as lauryl bromide, aralkyl halides like benzyl and phenethyl bromides.

Methods of treatment of this invention include those glutamate-mediated maladies wherein inhibition of glutamate release is desireable. These methods may be characterized as methods for inhibiting or limiting neuronal glutamate release in a mammal, the method comprising administering to the mammal, preferably to a human patient, a pharmaceutically effective amount of a compound of this invention, or a pharmaceutically effective salt thereof.

As such, these compounds may be useful in the treatment of several diseases such as anxiety, depression, schizophrenia, sexual dysfunction, cognitive deficits resulting from neurodegenerative diseases including Alzheimer's Disease, nausea and vomiting, epilepsy, sleep disorders, obesity, pain, addiction/withdrawal, urinary incontinence, prostate cancer, and ischemia resulting from acute stroke, transient ischemic attack, head and spinal trauma, fetal hypoxia, neuronal hypoxia, cardiac surgery or any other surgical technique which requires halting the blood flow for a period of time.

The methods of this invention are also useful in inhibiting or limiting the chronic neurodegenerative actions associated with Alzheimer's Disease, Huntington's Disease, Parkinson's Disease, epilepsy, amyotrophic lateral sclerosis, AIDS dementia as well as retinal diseases. Therefore, this invention also comprises methods of treatment for each of these maladies, the methods comprising administering to a mammal in need thereof a pharmaceutically effective amount of a compound of this invention, or a pharmaceutically acceptable salt thereof.

The compounds of this invention may also be used in the mediation or inhibition of glutamate activity associated with the maladies known as chronic, neuropathic or persistant pain, including its actions in fibromyalgia, postherpetic neuralgia, reflex sympathetic dystrophy, diabetic peripheral neuropathy, etc.

Of particular interest is methods of using the compounds of this invention to treat, prevent, limit, inhibit, delay or alleviate neurodegeneration in a mammal, the methods comprising administering to a mammal in need thereof a pharmaceutically effective amount of a compound of this invention, or a pharmaceutically acceptable salt thereof. These methods include those in which the neurodegenerative disease or disorder is acute or chronic. Included are those instances in which the neurodegeneration results from stroke, including thromboembolic stroke, focal ischemia, global ischemia and tranient ischemic attack. Also included are those neurodegenerative disorders such as ischemia resulting from a surgical technique involving prolonged halt of blood flow to the brain, head or spinal trauma, or hypoxia, including fetal hypoxia.

For their ability to inhibit, prevent or limit further neural degradation in the hypoxic and ischemic events of the maladies described above, the methods of treatment of this invention may also be characterized as methods for providing or inducing neuroprotection in a mammal, as their activity reduces or inhibits the glutamate-mediated or glutamate-related degeneration which would naturally occur.

The compound of formula I can be prepared by conventional chemical methods which are well known to those skilled in the art of chemistry using chemicals that are either commercially available or readily prepared following standard literature procedures. For example, the compounds may be synthesized in four steps (Scheme 1) starting from the appropriate phenylalanine, phenylglycine or heteroaryl-substituted alanine or heteroaryl-substituted glycine which has been protected on the nitrogen atom with a suitable protecting group such as the t-butoxycarbonyl group (BOC).

This material is coupled to the appropriately substituted arylpiperazine or aralkyl piperazine using a suitable coupling catalyst, such as dicyclohexylcarbodiimide (DCC) to afford compound 1. Removal of the BOC group under acidic conditions followed by reduction using an appropriate reducing agent such as lithium aluminum hydride or a borane complex leads to the penultimate intermediate 3. Subsequent acylation of 3 with a suitable acylating agent such as adamantane-1-carboxylic acid chloride or noradamantyl-3-carboxylic acid chloride gives compounds of formula I, which are isolated as acceptable salts.

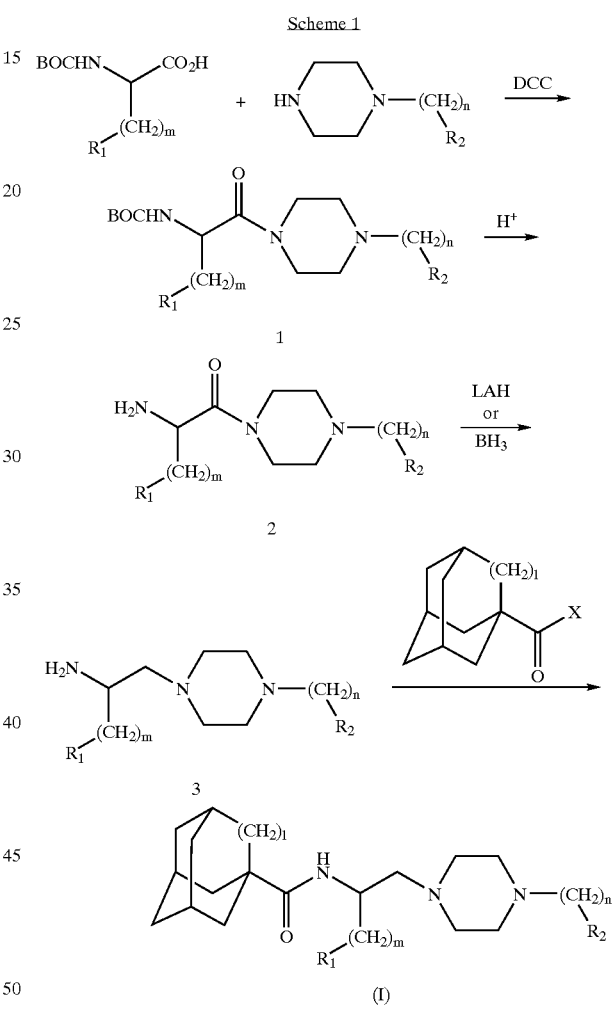

In cases where the $R_2$ grouping is not compatible with the reductive conditions required for the conversion of intermediate 2 to intermediate 3, it may be introduced after the reduction of the amide by initially protecting the NH group of the piperazine with a benzyl moiety (Scheme 2). This benzyl group can then be removed under catalytic hydrogenation conditions and the $R_2$ group incorporated into the molecule to give the final products.

The starting materials required for the synthesis of the compounds of formula I are either commercially available or readily obtained using conventional methods described in the literature. The preparative method described above is not meant to be restrictive but only illustrative since other methods of preparing the compounds of formula I may be obvious to those skilled in the art of chemistry. For example, while numerous, N-protected amino acids are commercially available, the protecting group may alternatively be introduced onto an amino acid using conventional methods which are well described in the literature. Other protecting groups such as carbobenzyloxy (CBZ) may be employed to protect the nitrogen grouping in the first step of the synthesis and many other coupling catalysts may serve to effect the reaction. Exact reagents required to de-protect the amine group of intermediate 1 once the coupling has been effected will depend on the protecting group used and the substituents present in the molecule. Other reducing agents besides LAH or borane may serve to accomplish the reduction of intermediate 2. Finally, the introduction of the acyl-adamantyl or acyl-noradamantyl group may be accomplished according to the general method described in Scheme 1 using one of many possible acylating derivatives, which include but are not limited to acid halides (e.g., acid chloride), anhydrides and activated esters and amides or through the use of adamantyl- or noradamantyl carboxylic acid and an appropriate coupling catalyst.

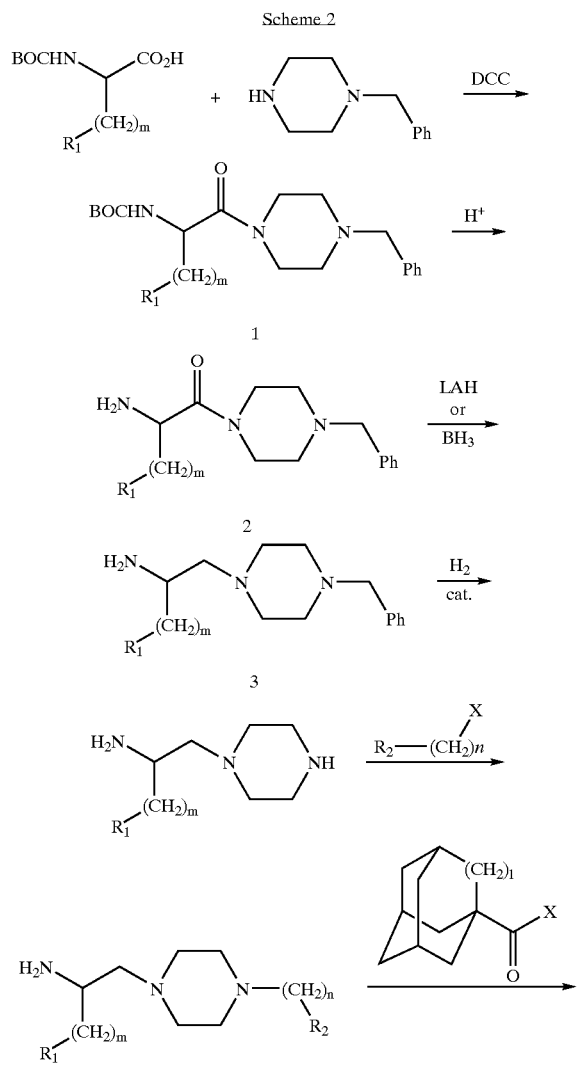

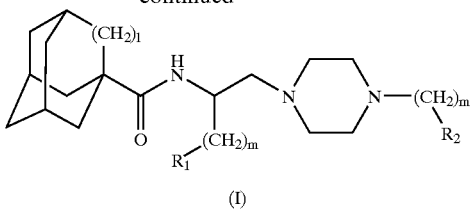

Since numerous chirally pure amino acids and protected amino acids are either commercially available or known in the literature, the pure optical isomers of the compounds of formula I may be obtained stereospecifically by beginning the synthesis with chirally pure starting materials. Alternatively, the optical isomers of the compounds of formula I may be obtained by conventional separation methods which are well known to those skilled in the art of synthetic chemistry. These methods include but are not restricted to crystallization of a mixture of diastereomeric salts, enzymatic resolution, chromatography of one of the intermediates or the final product on a chiral column, or formation and separation of a diastereomeric mixture followed by conversion back to the chirally pure material.

The following examples are included for illustrative purposes only and are not intended to be considered as limiting to this disclosure in any way.

EXAMPLE 1

(R)-N-[1-(Phenylmethyl)-2-[4(phenylmethyl)-1-piperazinyl]ethyl]tricyclo[3.3.1.1$^{3,7}$)]decane-1-carboxamide Dihydrochloride Dihydrate (R)-Phenylalanine-N-[4phenylmethyl)-1-piperizinyl]carboxamide Dihydrochloride D-Phenylalanine-N-t-butoxycarboxamide (13.25 g, 50 mmol) and 1-benzylpiperazine (8.8 g, 50 mmol) were dissolved in 125 mL of dry dichloromethane and cooled in an ice bath. The stirred mixture was then treated with a solution of diethylcyanophosphonate (8.97 g, 55 mmol) in 50 mL of dry dichloromethane over a period of 45 minutes. A solution of N-methylmorpholine (5.55 g, 55 mmol) in 50 mL of dry dichloromethane was then added over a period of one hour. The resulting reaction mixture was stirred overnight, during which time it came up to room temperature. The solution was then washed with 100 mL of 10% aqueous potassium carbonate, dried over anhydrous sodium sulfate, and concentrated on a rotary evaporator to yield 26 g of the crude intermediate BOC-(R)-phenylalanine-N-(4-benzyl-1-piperazinyl)carboxamide. This oil was dissolved in 200 mL of dichloromethane and treated with a 4.6 N solution of HCl in ethyl acetate (350 mL). After stirring at room temperature for one hour (at which time $CO_2$ evolution ceased), 250 mL of dry diethyl ether was added. The desired dihydrochloride salt of (R)-phenylalanine-N-[(4-phenylmethyl)1-piperazinyl]-carboxamide (18.9 g, 95%) precipitated and was isolate by filtration, washed with diethyl ether, and dried in vacuo: mp=140–150° C.; $[\alpha\text{-}D]^{25}=-3.7°$ (c=1, MeOH); MS m/z=323 (M$^+$).

(R)-[1-(Phenylmethyl)-2-[(4-phenylmethyl)-1-piperazinyl] ethyl]amine.

A solution of (R)phenylalanine-N-[(4-phenylmethyl)-1-piperazinyl]carboxamide dihydrochloride (18.8 g, 47.4 mmol) in 230 mL of 1 M borane/tetrahydrofuran was refluxed with stirring for four hours under a nitrogen atmosphere. The resulting mixture was cooled in an ice bath and quenched by slow addition of 150 mL of 2N aqueous HCl. The resulting mixture was then refluxed with stirring overnight. The tetrahydrofuran was removed under reduced pressure. The filtrate was washed with five 50 mL portions of dichloromethane and then made strongly basic with 50% aqueous sodium hydroxide solution. The resulting alkaline mixture was then extracted with three 100 mL portions of dichloromethane. The combined organic layers were dried over anhydrous sodium sulfate and concentrated on a rotary evaporator to yield the desired (R)-1-(phenylmethyl)-2-[(4phenylmethyl)-1-piperazinyl]ethyl]amine (17.1 g, 95%) as a yellow oil which was used without further purification. A sample of this oil was converted to the trihydrochloride sesquihydrate salt with ethyl acetate/HCl for characterization: m.p.=183–185° C.; $[\alpha\text{-D}]^{25}$=−27.7 (c=1, MeOH); MS m/z=309 (M$^+$).

Analysis for $C_{20}H_{25}N_3O.3$ HCl. 1½$H_2O$

Calculated: C, 53.83; H, 7.40; N, 9.42.

Found: C, 54.22; H, 7.11; N, 9.24.

(R)-N-[1-(Phenylmethyl)-2-[4-(phenylmethyl)-1-piperazinyl]-ethyl]tricyclo-[3.3.1.1$^{3,7}$)]-decane-1 carboxamide Dihydrochloride Dihydrate To an ice-cooled solution of 1-adamantanecarboxylic acid (5.1 g, 50 mmol) and (R)-[1-(phenylmethyl)-2-[(4-phenylmethyl)-1-piperazinyl]ethyl]amine (9.6 g, 25 mmol) in 60 mL of dry dichloromethane was added, with stirring, diethylcyanophosphonate (4.1 g, 25 mmol) over a period of thirty minutes. Upon completed addition, N-methylmorpholine (2.53 g, 25 mmol) was added and the resulting mixture was stirred overnight during which time it came up to room temperature. The reaction mixture was then washed with 100 mL of 10% aqueous potassium carbonate solution followed by 100 mL of water. The resulting organic layer was dried over anhydrous sodium sulfate and concentrated on a rotary evaporator. The desired product was isolated by chromatography on silica gel using a gradient of ethyl acetate and hexane and then converted to its dihydrochloride dihydrate salt (6.30 g, 44%) with HCl/ethyl acetate: mp=261–263° C.; $[\alpha\text{-D}]^{25}$=−12.5° (c=1, MeOH); CIMS m/z=472 (MH$^+$).

Analysis for $C_{31}H_{41}N_3O.2$ HCl.2 $H_2O$

Calculated: C, 64.12; H, 8.16; N, 7.24.

Found: C, 63.92; H, 8.30; N, 6.90.

EXAMPLE 2

(S)-N-[1-(Phenylmethyl)-2-[4-(phenylmethyl)-1-piperazinyl]ethyl]tricyclo[3.3.1.1$^{3,7}$)]-decane-1-carboxamide Dihydrochloride Dihydrate Beginning with L-phenylalanine-N-t-butoxycarboxamide, (S)-N-[1-(phenylmethyl)-2-[4-(phenylmethyl)-1-piperazinyl]ethyl]tricyclo[3.3.1.1.$^{3,7}$)]-decane-1-carboxamide was prepared using a synthetic sequence identical to that described for the synthesis of Example 1. It was isolated as its dihydrochloride dihydrate salt in 9% overall yield: mp 263–266° C.; $[\alpha\text{-D}]^{25}$=+11.3 (c=1.03, MeOH); CIMS m/z=472 (MH$^+$).

Analysis for $C_{31}H_{41}N_3O.2$ HCl.2 $H_2O$

Calculated: C, 64.12; H, 8.16; N, 7.24.

Found: C, 64.13; H, 7.86; N, 7.27.

EXAMPLE 3

(R)-N-[1-(Phenylmethyl)-2-[4-(2-pyrimidinyl)-1-piperazinyl]ethyl]tricyclo[3.3.1.1$^{3,7}$)]-decane-1-carboxamide Hemihydrate The compound of Example 1 (4.5 g, 7.84 mmol) was hydrogenated over 10% Pd/C (1 g) in 200 mL of ethanol on a Parr shaker at a pressure of 36 psi overnight. The catalyst was removed by filtration through Celite and the mixture concentrated on a rotary evaporator to yield the crude (R)-N-[1-(phenylmethyl)-2-[4(2-pyrimidinyl)-1-piperazinyl]ethyl]tricyclo[3.3.1.1$^{3,7}$)]-decane-1-carboxamide (2.8 g) as an oil. This oil was dissolved in 50 mL of dry dimethylformamide. To the stirred solution was added 2-chloropyrimidine (1.05 g, 9.2 mmol), anhydrous potassium carbonate (12.4 g, 90 mmol), and triethylamine (1 mL), and the resulting mixture was heated at 70° C. overnight. The DMF was removed on a rotary evaporator and the residue was triturated with water. The resulting precipitate was washed with water, air-dried, and recrystallized from 50% aqueous methanol to yield the desired compound as a hemihydrate: mp 172–175° C.; $[\alpha\text{-D}]^{25}$=−9.7° (c=1.07, MeOH); CIMS m/z=460 (MH$^+$).

Analysis for $C_{28}H_{35}N_5O$.½ $H_2O$

Calculated: C, 71.76; H, 8.17; N, 14.95.

Found: C, 71.90; H, 8.02; N, 14.82.

EXAMPLE 4

(S)-N-[1-(Phenylmethyl)-2-[4-(2-pyrimidinyl)-1-piperazinyl]ethyl]tricyclo[3.3.1.1$^{3,7}$)]-decane-1-carboxamide Beginning with the compound of Example 2, (S)-N-[1-(phenylmethyl)-2-[4-(2-pyrimidinyl)-1-piperazinyl]ethyl]tricyclo[3.3.1.1$^{3,7}$)]-decane-1-carboxamide was prepared using a synthetic sequence identical to that described for the synthesis of Example 3. It was isolated in 78% overall yield: mp 172–175° C.; $[\alpha\text{-D}]^{25}$=+7.20 (c=1.03, MeOH); CIMS m/z=460 (MH$^+$).

Analysis for $C_{28}H_{37}N_5O$

Calculated: C, 73.17; H, 8.11; N, 15.24.

Found: C, 72.87; H, 7.90; N, 15.00.

EXAMPLE 5

(R)-N-[1-(Phenylmethoxymethyl)-2-[4-(phenylmethyl)-1-piperazinyl]ethyl]tricyclo-[3.3.1.1$^{3,7}$)]-decane-1-carboxamide Dihydrochloride Dihydrate Beginning with D-O-benzylserine-N-t-butoxycarboxamide, (R)-N-[1-((phenylmethoxy)-methyl)-2-[4-(phenylmethyl)-1-piperazinyl]ethyl]-tricyclo-[3.3.1.1$^{3,7}$)]-decane-1-carboxamide was prepared using a synthetic sequence identical to that described for the synthesis of Example 1. It was was converted to its dihydrochloride dihydrate salt with ethyl acetate/HCl and isolated in 5% overall yield: mp 140–142° C.; $[\alpha\text{-D}]^{25}$=+19.0 (c=0.98, MeOH); CIMS m/z=502 (MH$^+$).

Analysis for $C_{32}H_{43}N_3O_2.2$ HCl.2 $H_2O$
Calculated: C, 62.94; H, 8.08; N, 6.88.
Found: C, 62.74; H, 8.07; N, 6.86.

EXAMPLE 6

(R)-Adamantane-1-carboxylic acid[1-(phenylmethyl)-2-[4-(2-methoxyphenyl)piperazinyl]ethyl]-amide Hemifumarate Hemihydrate (R)-[1-(Phenylmethyl )-2-[4-(2methoxyphenyl)-1-piperazinyl]-2-oxo-ethyl]-carbamic acid tert-butyl ester.

To a 0° C. solution of D-phenylalanine-N-t-butoxy-carboxamide (10.0 g, 37.7 mmol), 1-hydroxybenzotriazole (8.66 g, 64.1 mmol) and 1-(3-dimethylaminopropyl)-3-ethylcarbodiimide hydrochloride (7.20 g, 37.7 mmol) in dry dimethylformamide (50 mL) under a nitrogen atmosphere, was added 1-(2-methoxyphenyl)-piperazine (9.50 g, 41.5 mmol), followed by N-methylmorpholine (7.62 g, 75.4 mmol). The resulting mixture was stirred under nitrogen overnight, during which time it came up to room temperature. The reaction mixture was diluted with ethyl acetate and then washed with 0.1 N aqueous HCl, saturated aqueous sodium bicarbonate and saturated sodium chloride solution. The combined organic layers dried over anhydrous sodium sulfate and concentrated under reduced pressure to yield the desired product (16.57 g, 99% yield) as a yellow oil which was pure enough to use without further purification: $[\alpha\text{-D}]^{25}=-9.0$ (c=1, MeOH); MS m/z=439 ($M^+$).

Analysis for $C_{25}H_{33}N_{34}$
Calculated: C, 68.31; H, 7.57; N, 9.56.
Found: C, 68.09; H, 7.17; N, 9.46.

(R)-1-(Phenylmethyl)-2-[4-(2-methoxyphenyl)-1-piperazinyl]-ethyl)amine

A solution of (R)-[1-(phenylmethyl)-2-[4-(2-methoxyphenyl)-1-piperazinyl]-2-oxo-ethyl]-carbamic acid tert-butyl ester (16.37 g, 37.3 mmol) in a mixture of dioxane (150 mL)/4N aqueous HCl (150 mL) was stirred at room temperature for 6 hours. The reaction mixture was then concentrated under reduced pressure and the aqueous mixture was extracted with diethyl ether. The combined organic extracts were dried over anhydrous sodium sulfate and concentrated under reduced pressure to yield the desired (R)-[1-(phenylmethyl)-2-[4-(2-methoxyphenyl)-1-piperazinyl]-2-oxoethyl]amine hydrochloride (14.0 g, 100% yield) as an off-white solid, which was used in the next step without further purification.

To a solution of (R)-[1-(phenylmethyl)-2-[4-(2-methoxyphenyl)-1-piperazinyl]-2-oxo-ethyl]amine hydrochloride (14 g, 37.3 mmol) and triethylamine (7.53 g, 74.6 mmol) in anhydrous tetrahydrofuran (150 mL) under a nitrogen atmosphere was added, dropwise, a 1M solution of borane in tetrahydrofuran (131 mL, 130.6 mmol). The resulting mixture was stirred at reflux for three hours, then allowed to stir at room temperature overnight. The resulting mixture was treated with 2N aqueous HCl (300 mL) for two hours and the layers were separated. The acidic aqueous layer was washed with ethyl acetate, made basic with 50% aqueous sodium hydroxide, and extracted with ethyl acetate. The combined organic layers were washed with saturated aqueous sodium chloride solution, dried over anhydrous sodium sulfate and concentrated under reduced pressure. The desired product (11.0 g, 91.0% yield)was isolated as an off-white solid: m.p.=95–97° C.; $[\alpha\text{-D}]^{25}=-36.7$ (c=1, MeOH); FAB MS m/z=326 ($MH^+$).

Analysis for $C_{20}H_{27}N_3O$
Calculated: C, 73.80; H, 8.37; N, 12.77.
Found: C, 73.15; H, 8.34; N, 12.68.

(R)-Adamantane-1-carboxylic acid[1-(phenylmethyl)-2-[4-(2methoxy-phenyl)-piperazinyl]ethyl]-amide Hemifumarate Hemihydrate To a solution of (R)-1-(phenylmethyl)-2-[4-(2-methoxyphenyl)-1-piperazinyl)ethyl]amine (0.25 g, 0.77 mmol) and triethylamine (0.16 g, 1.54 mmol) in anhydrous dichloromethane (15 mL) under a nitrogen atmosphere at 0 C. was added a solution of 1-adamantane-carboxylic acid chloride (0.17 g, 0.84 mmol) in dichloromethane (5 mL). The resulting solution was allowed to stir overnight under nitrogen, during which time it came up to room temperature. The reaction mixture was then concentrated under reduced pressure, diluted with ethyl acetate and washed with water. The organic layer was dried over anhydrous sodium sulfate and concentrated under reduced pressure. The desired product was purified by flash chromatography on silica gel (ethyl acetate/hexane) and converted to its hemifumarate hemihydrate salt with fumaric acid/ethanol to yield 0.30 g (71% yield) as a white solid: m.p. 153–155° C.; $[\alpha\text{-D}]^{25}=-9.0$ (c=1, MeOH); MS m/z=487 ($M^+$).

Analysis for $C_{31}H_{41}N_3O_2.\frac{1}{2} C_4O_4.\frac{1}{2} H_2O$
Calculated: C, 71.45; H, 8.00; N, 7.57.
Found: C, 71.26; H, 8.05; N, 7.42.

EXAMPLE 7

(S)-Adamantane-1-carboxylic acid[1phenylmethyl)-2-[4-(2-methoxyphenyl)-piperazinyl]ethyl]-amide Hemifumarate Hydrate This compound was prepared using an identical synthetic sequence to that described for Example 6 starting with L-phenylalanine-N-t-butoxy-carboxamide. The overall yield was 61% and the compound (an off-white solid) was isolated as the hemifumarate hydrate salt: m.p.=157 –159° C.; $[\alpha\text{-D}]^{25}=+9.5$ (c=1, MeOH); FAB MS m/z=488 ($MH^+$).

Analysis for $C_{31}H_{41}N_3O_2.\frac{1}{2} C_4O_4.\frac{1}{2} H_2O$
Calculated: C, 70.31; H, 8.05; N, 7.45.
Found: C, 70.21; H, 8.04; N, 7.11.

In Vitro Data

Affinity for the serotonin $5\text{-HT}_{1A}$ receptor was established by assaying the test compound's ability to displace [$^3$H]-8-OH-DPAT from its binding site on the receptor complex in rat hippocampal membrane homogenates according to the method described in U.S. Pat. No. 5,482,940. The compounds of this invention displayed high affinity for the $5\text{-HT}_{1A}$ receptor, as exemplified by the data given in Table 1.

Some of the compounds of this invention displayed serotonin $5\text{-HT}_{1A}$ agonist activity, as measured by the test compounds's ability to stimulate the binding of [$^{35}$S]-GTPγS to the $5\text{-HT}_{1A}$ receptor-G protein complex in CHO cells stably transfected with the human $5HT_{1A}$ receptor following a variation of the procedure described by Lazerino and Birdsall (*Br. J. Pharmacol.*, 109, 1120 (1993)). Data are given in Table 1. Data are presented as the percent of

TABLE 1

| Example | $5\text{-}HT_{1A}$ Affinity ($IC_{50}$) | $5\text{-}HT_{1A}$ Agonist Activity (GTPγS) | | $5\text{-}HT_{1A}$ Antagonist Activity (GTPγS) | |
|---|---|---|---|---|---|
| | | % Agonist Activity | $EC_{50}$ | % Antagonist Activity | $EC_{50}$ |
| 1 | 2.3 nM | | | 100% | 36 nM |
| 2 | 0.70 nM | 51% | 21 nM | | |
| 3 | 0.43 nM | 100% | 2.0 nM | | |
| 4 | 1.0 nM | 99% | 2.4 nM | | |
| 5 | 62 nM | 49% | 77 nM | | |
| 6 | 0.21 nM | 76% | 2.0 nM | | |
| 7 | 0.70 nM | 85% | 2.0 nM | | | agonist activity observed relative to the effect obtained with the 5-$HT_{1A}$ full agonist 8-OH-DPAT and the corresponding $EC_{50}$ value. As can be seen from Table 1, the compounds of this invention are potent 5-$HT_{1A}$ ligands which display agonist and partial agonist activity in the $GTP_\gamma S$ assay.

Some of the compounds of this invention displayed serotonin 5-$HT_{1A}$ antagonist activity, as measured by the test compound's ability to block the stimulation of the binding of [$^{35}$S]-GTP S to the 5-$HT_{1A}$ receptor-G protein complex induced by the 5-$HT_{1A}$ full agonist 8-OH-DPAT in CHO cells stably transfected with the human 5-$HT_{1A}$ receptor following a variation of the procedure described by Lazerino and Birdsall (Br. J. Pharmacol., 109, 1120 (1993)). Data are given in Table 1. As can be seen from Table 1, some of the compounds of this invention are potent 5-$HT_{1A}$ ligands which display antagonist activity in the GTP S assay.

These activities make the compounds of this invention useful for the treatment of several diseases such as anxiety, depression, schizophrenia, sexual dysfunction, cognitive deficits resulting from neurodegenerative diseases like Alzheimer's Disease, nausea and vomiting, epilepsy, sleep disorders, obesity, pain, addiction/withdrawal, urinary incontinence, prostate cancer, and ischemia resulting from acute stroke, transient ischemic attack, head and spinal trauma, fetal hypoxia, cardiac surgery or any other surgical technique which requires halting the blood flow for a period of time, and chronic neurodegenerative diseases such as Alzheimer's Disease, Huntington's Disease, Parkinson's Disease, amyotrophic lateral sclerosis, AIDS dementia as well as retinal diseases.

Pharmaceutical Composition

This invention also comprises pharmaceutical compositions comprising pharmaceutically effective amounts of one or more compounds of this invention, or a pharmacetically acceptable salt thereof, and one or more pharmaceutically acceptable carriers or excipients. The pharmaceutically effective amount of these compounds will be understood to be an amount which provides an effective degree of neuroprotection or treats, inhibits or limits the neurodegeneration in question. In humans, a daily dosage of from about 100 mg to about 1,500 mg per day may be administered, preferably between about 300 mg and about 1,200 mg per day, more preferably between about 500 mg and 1,000 mg per day. These dosages may be administered in a single administration or divided into multiple doses for sequential administration.

The compounds of the present invention may be administered orally or parentally, neat or in combination with conventional pharmaceutical carriers. Applicable solid carriers can include one or more substances which may also act as flavoring agents, lubricants, solubilizers, suspending agents, fillers, glidants, compression aids, binders, tablet-disintegrating agents or encapsulating materials. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets may contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins. Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g., cellulose derivatives, preferably sodium carboxymethyl cellulose solution), alcohols (including monohydric alcohols and polyhydric alcohols, e.g., glycols) and their derivatives, and oils (e.g., fractionated coconut oil and arachis oil). For parenteral administration, the carrier can also be an oily ester such as ethyl oleate and isopropyl myristate. Sterile liquid carriers are used in sterile liquid form compositions for parenteral administration. Liquid pharmaceutical compositions, which are sterile solutions or suspensions can be utilized by, for example, intramuscular, intraperitoneal or subcutaneous injection. Sterile solutions can also be administered intravenously. Oral administration may be either in liquid or solid composition form. Preferably, the pharmaceutical compositions containing the present compounds are in unit dosage form, e.g., as tablets or capsules. In such form, the composition is subdivided in unit dosages containing appropriate quantities of the active ingredients. The unit dosage forms can be packaged compositions, for example, packaged powders, vials, ampoules, prefilled syringes or sachets containing liquids. Alternatively, the unit dosage form can be, for example, a capsule or tablet itself, or it can be the appropriate number of any such compositions in package form. The therapeutically effective dosage to be used in the treatment of a specific disease or condition must be subjectively determined by the attending physician. The variables involved include the specific condition(s) being treated and the size, age and response pattern of the patient.

The present invention may be embodied in other specific forms without departing from the spirit and essential attributes thereof and accordingly, reference should be made to the appended claims, rather than to the foregoing specification, as indicating the scope of the invention.

What is claimed:

1. A compound of the formula:

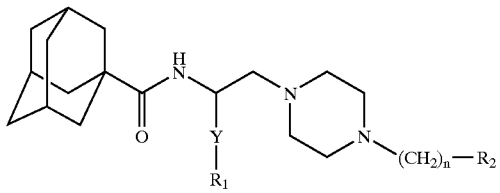

wherein:
Y is selected from —CH$_2$— or —CH$_2$—O—CH$_2$—;
n is selected from the integer 0 or 1;
R$_1$ is phenyl optionally substituted with F, Cl, Br, I, —OH, —NH$_2$, —CO$_2$H, —CO$_2$—C$_1$-C$_6$ alkyl, —CN, —NO$_2$, C$_1$-C$_6$ alkyl, C$_1$-C$_6$ alkoxy, C$_2$-C$_6$ alkenyl, C$_1$-C$_6$ perhaloalkyl or C$_1$-C$_6$ perhaloalkoxy;
R$_2$ is phenyl, pyrimidinyl, pyridyl, pyridazinyl, or pyrazinyl optionally substituted with F, Cl, Br, I, —OH, —NH$_2$, —CO$_2$H, —CO$_2$—C$_1$-C$_6$ alkyl, —CN, —NO$_2$, C$_1$-C$_6$ alkyl, C$_2$-C$_6$ alkenyl, C$_1$-C$_6$ perhaloalkyl, or C$_1$-C$_6$ perhaloalkoxy;
and the optical isomers or a pharmaceutically acceptable salt thereof.

2. A compound of claim 1 wherein:
R$_1$ is phenyl optionally substituted with F, Cl, Br, I, —OH, —NH$_2$, C$_1$-C$_6$ alkyl, C$_1$-C$_6$ alkoxy, C$_1$-C$_6$ perhaloalkyl or C$_1$-C$_6$ perhaloalkoxy;
R$_2$ is phenyl or pyrimidinyl optionally substituted with F, Cl, Br, I, —OH, —NH$_2$, —CO$_2$H, —CO$_2$—C$_1$-C$_6$ alkyl, —CN, —NO$_2$, C$_1$-C$_6$ alkyl, C$_2$-C$_6$ alkenyl, C$_1$-C$_6$ perhaloalkyl, or C$_1$-C$_6$ perhaloalkoxy;
and the optical isomers or a pharmaceutically acceptable salt thereof.

3. A compound of claim 1 wherein:
R$_1$ is phenyl optionally substituted with F, Cl, Br, I, C$_1$-C$_6$ alkyl, C$_1$-C$_6$ alkoxy, C$_1$-C$_6$ perhaloalkyl or C$_1$-C$_6$ perhaloalkoxy;
R$_2$ is phenyl or pyrimidinyl, optionally substituted with F, Cl, Br, I, C$_1$-C$_6$ alkyl, C$_1$-C$_6$ perhaloalkyl, or C$_1$-C$_6$ perhaloalkoxy;
and the optical isomers or a pharmaceutically acceptable salt thereof.

4. A compound of claim 1 which is (R)-N-[1-(Phenylmethyl)-2-[4-(phenylmethyl)-1-piperazinyl]ethyl]tricyclo[3.3.1.1$^{3,7}$)]-decane-1-carboxamide Dihydrochloride Dihydrate.

5. A compound of claim 1 which is (R)-N-[1-(Phenylmethyl)-2-[4-(phenylmethyl)-1-piperazinyl]ethyl]tricyclo-[3.3.1.1$^{3,7}$)]-decane-1-carboxamide Dihydrochloride Dihydrate.

6. A compound of claim 1 which is (S)-N-[1-(Phenylmethyl)-2-[4-(phenylmethyl)-1-piperazinyl]ethyl]tricyclo[3.3.1.1$^{3,7}$)]-decane-1-carboxamide Dihydrochloride Dihydrate.

7. A compound of claim 1 which is (R)-N-[1-(Phenylmethyl)-2-[4-(2-pyrimidinyl)-1-piperazinyl]ethyl]tricyclo[3.3.1.1$^{3,7}$)]-decane-1-carboxamide Hemihydrate.

8. A compound of claim 1 which is (S)-N-[1-(Phenylmethyl)-2-[4-(2-pyrimidinyl)-1-piperazinyl]ethyl]tricyclo[3.3.1.1$^{3,7}$)]-decane-1-carboxamide.

9. A compound of claim 1 which is (R)-N-[1-((Phenylmethoxy)methyl)-2-[4-(phenylmethyl)-1-piperazinyl]ethyl]tricyclo-[3.3.1.1$^{3,7}$)]-decane-1-carboxamide Dihydrochloride Dihydrate.

10. A compound of claim 1 which is (R)-Adamantane-1-carboxylic acid [1-(phenylmethyl)-2-[4-(2-methoxyphenyl)-piperazinyl]ethyl]-amide Hemifumarate Hemihydrate.

11. A compound of claim 1 which is (S)-Adamantane-1-carboxylic acid [1-(phenylmethyl)-2-[4-(2-methoxyphenyl)-piperazinyl]ethyl]-amide Hemifumarate Hemihydrate.

12. A compound of claim 1 which is (S)-Adamantane-1-carboxylic acid [1-(phenylmethyl)-2-[4-(2-methoxyphenyl)-piperazinyl]ethyl]-amide Hemifumarate Hemihydrate.

13. A pharmaceutical composition comprising
a) a pharmaceutically effective amount of at least one compound of claim 1 or a pharmaceutically acceptable salt thereof; and
b) one or more pharmaceutically acceptable carriers or excipients.

* * * * *